US012066420B2

(12) United States Patent
Qin et al.

(10) Patent No.: US 12,066,420 B2
(45) Date of Patent: Aug. 20, 2024

(54) ANALYZER AND CONTROL METHOD THEREOF, DETECTION SYSTEM, AND STORAGE MEDIUM

(71) Applicant: BOE Technology Group Co., Ltd., Beijing (CN)

(72) Inventors: Qin Qin, Beijing (CN); Jing Li, Beijing (CN); Yahua Yuan, Beijing (CN); Hongquan Li, Beijing (CN); Mengli Feng, Beijing (CN); Yufan Zhang, Beijing (CN); Jing Zhao, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 360 days.

(21) Appl. No.: 17/623,939

(22) PCT Filed: Mar. 6, 2020

(86) PCT No.: PCT/CN2020/078208
§ 371 (c)(1),
(2) Date: Dec. 30, 2021

(87) PCT Pub. No.: WO2021/174528
PCT Pub. Date: Sep. 10, 2021

(65) Prior Publication Data
US 2022/0357307 A1 Nov. 10, 2022

(51) Int. Cl.
*G01N 33/04* (2006.01)
*G01N 21/27* (2006.01)
(52) U.S. Cl.
CPC ............. *G01N 33/04* (2013.01); *G01N 21/27* (2013.01)

(58) Field of Classification Search
None
See application file for complete search history.

(56) References Cited

U.S. PATENT DOCUMENTS 11,913,907 B2 * 2/2024 Valster ................... A61M 1/06
2004/0120861 A1 6/2004 Petroff
(Continued)

FOREIGN PATENT DOCUMENTS

CN 203479807 U 3/2014
CN 105301228 A 2/2016
(Continued)

OTHER PUBLICATIONS

Oct. 20, 2022—(EP) Extended European Search Report Appn 20923456.6.

*Primary Examiner* — Peter J Macchiarolo
*Assistant Examiner* — Jermaine L Jenkins
(74) *Attorney, Agent, or Firm* — Banner & Witcoff, Ltd.

(57) ABSTRACT

An analyzer and a control method thereof, a detection system, and a storage medium are provided. The control method of the analyzer includes: determining whether the analyzer obtains an analysis parameter corresponding to a detection chip used for detection: requesting and obtaining the analysis parameter in a case of being determined that the analyzer does not obtain the analysis parameter; and performing detection on the detection chip and analyzing a substance to be analyzed contained in the detection chip by using the analysis parameter to obtain analysis data of the substance to be analyzed in a case of being determined that the analyzer obtains the analysis parameter.

19 Claims, 6 Drawing Sheets

(56) References Cited

U.S. PATENT DOCUMENTS

| | | | |
|---|---|---|---|
| 2013/0126597 A1 | 5/2013 | Chang et al. | |
| 2017/0108435 A1* | 4/2017 | Anctil | G01N 21/645 |
| 2017/0218436 A1* | 8/2017 | Azimi | B01L 3/50273 |
| 2019/0086431 A1 | 3/2019 | Isaacson et al. | |
| 2020/0393376 A1* | 12/2020 | Orbach | G16H 20/60 |

FOREIGN PATENT DOCUMENTS

| | | | |
|---|---|---|---|
| CN | 106226390 A * | 12/2016 | |
| CN | 106290281 A | 1/2017 | |
| CN | 106483283 A | 3/2017 | |
| CN | 107024584 A | 8/2017 | |
| CN | 206470275 U | 9/2017 | |
| CN | 206757357 U | 12/2017 | |
| CN | 207096261 U | 3/2018 | |
| CN | 108572153 A * | 9/2018 | |
| CN | 209400423 U | 9/2019 | |
| JP | 6502137 B2 | 10/2016 | |
| WO | 2017044691 A1 | 3/2017 | |

\* cited by examiner

ANALYZER AND CONTROL METHOD THEREOF, DETECTION SYSTEM, AND STORAGE MEDIUM

The application is a U.S. National Phase Entry of International Application No. PCT/CN2020/078208 filed on Mar. 6, 2020, designating the United States of America. The present application claims priority to and the benefit of the above-identified application and the above-identified application is incorporated by reference herein in its entirety.

TECHNICAL FIELD

Embodiments of the present disclosure relate to an analyzer and a control method thereof, a detection system, and a storage medium.

BACKGROUND

In recent years, with improvement of living standards, people's requirements for a balanced and nutritious diet are getting higher and higher, especially for infants who take breast milk as the main source of nutrition. By detecting and analyzing the content of trace elements in breast milk, such as calcium, zinc, iron, lactose, and protein, mothers can be given appropriate nutritional dietary guidance to ensure the nutritional balance of breast milk.

SUMMARY

At least one embodiment of the present disclosure provides a control method of an analyzer, the analyzer is configured to perform detection on a detection chip based on an analysis parameter, the detection chip is configured to contain a substance to be analyzed for detection and analysis, and the control method comprises: determining whether the analyzer obtains the analysis parameter corresponding to the detection chip used for detection; requesting and obtaining the analysis parameter in a case of being determined that the analyzer does not obtain the analysis parameter; and performing detection on the detection chip and analyzing the substance to be analyzed contained in the detection chip by using the analysis parameter to obtain analysis data of the substance to be analyzed in a case of being determined that the analyzer obtains the analysis parameter.

For example, in the control method of the analyzer provided by an embodiment of the present disclosure, the analyzer comprises a communication interface, and obtaining the analysis parameter comprises: allowing the analyzer to establish signal connection with a parameter storage device storing the analysis parameter through the communication interface, and reading and storing the analysis parameter.

For example, in the control method of the analyzer provided by an embodiment of the present disclosure, the parameter storage device is a USB flash drive and the communication interface is a USB interface; or the parameter storage device is a first mobile terminal, and the communication interface is a wireless communication interface.

For example, in the control method of the analyzer provided by an embodiment of the present disclosure, the parameter storage device comprises a housing and further comprises a control circuit and a memory provided in the housing, the analysis parameter is stored in the memory, and the control circuit is configured to establish the signal connection and read the analysis parameter from the memory.

For example, in the control method of the analyzer provided by an embodiment of the present disclosure, in the case of being determined that the analyzer obtains the analysis parameter, the control method further comprises: prompting to check whether the analysis parameter currently obtained corresponds to the detection chip used for detection; and requesting to obtain a new analysis parameter in a case where the analysis parameter currently obtained does not correspond to the detection chip used for detection.

For example, in the control method of the analyzer provided by an embodiment of the present disclosure, the analysis parameter comprises a calculation curve for acquiring the analysis data based on detection data of the detection chip.

For example, in the control method of the analyzer provided by an embodiment of the present disclosure, the analyzer further comprises at least one micro switch, and the control method further comprises: detecting an operation applied to the micro switch, and generating a control signal according to the operation, wherein the control signal is used for an interaction process of the analyzer.

For example, in the control method of the analyzer provided by an embodiment of the present disclosure, the micro switch protrudes outwards from a surface of the analyzer and has a long strip shape, and the micro switch is configured to be capable of being operated in at least two directions; and generating the control signal according to the operation comprises: generating different control signals for interaction according to operations of the micro switch in different directions.

For example, in the control method of the analyzer provided by an embodiment of the present disclosure, the analyzer further comprises a display device, and the control method further comprises: displaying the analysis data through the display device, or allowing the display device to display different interactive operation interfaces according to the control signal.

For example, in the control method of the analyzer provided by an embodiment of the present disclosure, the analysis data comprises a plurality of items, and displaying the analysis data through the display device comprises: switching a display page of the display device according to the control signal so as to display different items in the analysis data.

For example, in the control method of the analyzer provided by an embodiment of the present disclosure, the analyzer further comprises a communication device, and the control method further comprises: allowing the analyzer to be in signal connection with a second mobile terminal through the communication device, and receiving the control signal provided by the second mobile terminal or providing the analysis data to the second mobile terminal.

For example, the control method of the analyzer provided by an embodiment of the present disclosure further comprises: determining whether to establish the signal connection between the analyzer and the second mobile terminal through the communication device, and selecting an operation mode.

For example, in the control method of the analyzer provided by an embodiment of the present disclosure, the second mobile terminal comprises a display function, and the control method further comprises: displaying the analysis data and/or an analysis result provided based on the analysis data through the second mobile terminal, or displaying an interactive operation interface through the second mobile terminal for generating the control signal.

For example, the control method of the analyzer provided by an embodiment of the present disclosure further comprises: performing equipment detection on the analyzer to determine whether the analyzer satisfies a condition for performing detection on the detection chip.

For example, in the control method of the analyzer provided by an embodiment of the present disclosure, the substance to be analyzed comprises a breast milk sample.

At least one embodiment of the present disclosure further provides an analyzer, and the analyzer comprises a detection portion and a control device; the detection portion is configured to perform detection on a detection chip and receive detection data of the detection chip; and the control device is configured to determine whether an analysis parameter corresponding to the detection chip used for detection is obtained and request to obtain the analysis parameter in a case where the analysis parameter is not obtained, and the control device is further configured to, in a case of being determined that the analysis parameter is obtained, allow the detection portion to perform detection on the detection chip to obtain the detection data, and analyze the detection data by using the analysis parameter to obtain analysis data of a substance to be analyzed contained in the detection chip.

For example, in the analyzer provided by an embodiment of the present disclosure, the analyzer comprises a communication interface, and the communication interface is configured to allow the analyzer to be in signal connection with a parameter storage device storing the analysis parameter, so as to allow the analyzer to read and store the analysis parameter.

For example, in the analyzer provided by an embodiment of the present disclosure, the communication interface is a USB interface or a wireless communication interface.

For example, in the analyzer provided by an embodiment of the present disclosure, the communication interface is further configured to be able to charge the analyzer.

For example, the analyzer provided by an embodiment of the present disclosure further comprises at least one micro switch, the control device is further configured to detect an operation applied to the micro switch and generate a control signal according to the operation, and the control signal is used for an interaction process of the analyzer.

For example, in the analyzer provided by an embodiment of the present disclosure, the micro switch protrudes outwards from a surface of the analyzer and has a long strip shape, and the micro switch is configured to be capable of being operated in at least two directions; and the control device is further configured to generate different control signals for interaction according to operations of the micro switch in different directions.

For example, the analyzer provided by an embodiment of the present disclosure further comprises a display device, and the display device is configured to display the analysis data or display different interactive operation interfaces according to the control signal.

For example, the analyzer provided by an embodiment of the present disclosure further comprises a communication device, and the communication device is configured to allow the analyzer to be in signal connection with a second mobile terminal, so as to allow the analyzer to receive a control signal provided by the second mobile terminal or allow the analyzer to provide the analysis data to the second mobile terminal.

For example, in the analyzer provided by an embodiment of the present disclosure, the control device comprises a processor and a memory, and the memory comprises one or more computer program modules; and the one or more computer program modules are stored in the memory and configured to be executed by the processor, and the one or more computer program modules comprise instructions for implementing the control method of the analyzer according to any one of the embodiments of the present disclosure.

At least one embodiment of the present disclosure further provides a detection system, and the detection system comprises the analyzer according to any one of the embodiments of the present disclosure and at least one detection chip.

At least one embodiment of the present disclosure further provides a detection system, the detection system comprises the analyzer according to any one of the embodiments of the present disclosure, at least one detection chip, and a parameter storage device, and the parameter storage device stores the analysis parameter and is configured to be in signal connection with the analyzer through a communication interface of the analyzer, so as to allow the analyzer to read and store the analysis parameter.

At least one embodiment of the present disclosure further provides a storage medium, used for storing non-transitory computer readable instructions, and the control method of the analyzer according to any one of the embodiments of the present disclosure is implemented upon the non-transitory computer readable instructions being executed by a computer.

BRIEF DESCRIPTION OF THE DRAWINGS

In order to clearly illustrate the technical solutions of the embodiments of the present disclosure, the drawings of the embodiments will be briefly described in the following. It is obvious that the described drawings are only related to some embodiments of the present disclosure and thus are not limitative to the present disclosure.

DETAILED DESCRIPTION

Figure 1:
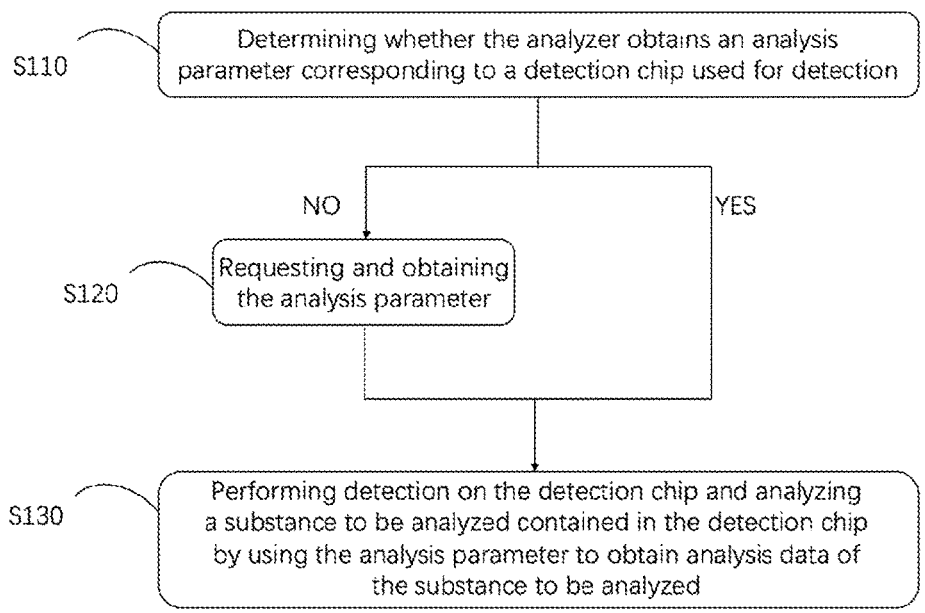
FIG. 1 is a flowchart of a control method of an analyzer provided by some embodiments of the present disclosure.

In order to make objects, technical details and advantages of the embodiments of the present disclosure apparent, the technical solutions of the embodiments of the present disclosure will be described in a clearly and fully understandable way in connection with the drawings related to the embodiments of the present disclosure. Apparently, the described embodiments are just a part but not all of the embodiments of the present disclosure. Based on the described embodiments of the present disclosure herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect," "connected," "coupled," etc., are not intended to define a physical connection or mechanical connection, but may include an electrical connection, directly or indirectly. "On," "under," "right," "left," and the like are only used to indicate relative position relationship, and when the position of the object which is described is changed, the relative position relationship may be changed accordingly.

At present, analysis devices used for detecting the substance content of various liquids (such as breast milk, milk, etc.) are mainly large-scale detection devices, which are expensive and complicated to operate and need special training for operators, and therefore these detection devices are mainly provided in public places such as hospitals or detection institutions. For the liquid that needs to be detected by these detection devices, because the detection process needs to be carried out in public places such as the above-mentioned hospitals or detection institutions, the detection process of the liquid is time-consuming and laborious, which greatly increases the detection cost of the liquid and is inconvenient for frequent detection of the liquid. However, it is particularly important to regularly monitor the substance content of breast milk, milk and other liquids which need to be detected regularly.

At least one embodiment of the present disclosure provides a control method of an analyzer, the analyzer is configured to perform detection on a detection chip based on an analysis parameter, and the detection chip is configured to contain a substance to be analyzed for detection and analysis. The control method of the analyzer includes: determining whether the analyzer obtains the analysis parameter corresponding to the detection chip used for detection; requesting and obtaining the analysis parameter in a case of being determined that the analyzer does not obtain the analysis parameter; and performing detection on the detection chip and analyzing the substance to be analyzed contained in the detection chip by using the analysis parameter to obtain analysis data of the substance to be analyzed in a case of being determined that the analyzer obtains the analysis parameter.

In the control method of the analyzer provided by the embodiments of the present disclosure, the detection chip is used to contain the substance to be analyzed, such as breast milk, milk, and other liquids which need to be detected, and the analyzer is used to perform detection and analysis on the detection chip based on the analysis parameter corresponding to or matching the detection chip. Thus, the analysis data of the substance to be analyzed can be accurately obtained, for example, the substance content of trace elements or the concentration value of specific components in the substance to be analyzed can be accurately obtained, so that the accuracy and reliability of the obtained analysis data may be improved while the detection process is simple and convenient to operate, thereby being helpful for the user to obtain accurate and reliable analysis results.

Hereinafter, some embodiments of the present disclosure will be described in detail with reference to the accompany drawings. It should be noted that the same reference numerals in different drawings are used to refer to the same described elements.

FIG. 1 is a flowchart of a control method of an analyzer provided by some embodiments of the present disclosure. For example, examples of the analyzer, the detection chip, the parameter storage device, or the like involved in the method may refer to descriptions of FIG. 3 to FIG. 6. For example, as illustrated in FIG. 1, the method includes the following steps S110-S130.

Step S110: determining whether the analyzer obtains an analysis parameter corresponding to a detection chip used for detection.

Step S120: requesting and obtaining the analysis parameter in a case of being determined that the analyzer does not obtain the analysis parameter.

Step S130: performing detection on the detection chip and analyzing a substance to be analyzed contained in the detection chip by using the analysis parameter to obtain analysis data of the substance to be analyzed in a case of being determined that the analyzer obtains the analysis parameter.

In the embodiments of the present disclosure, the analyzer is configured to perform detection on the detection chip based on the analysis parameter, and the detection chip is configured to contain the substance to be analyzed for detection and analysis.

Because there may be differences in the materials of different production batches of detection chips, and accordingly, there may be differences in the biological or chemical reaction conditions and reaction results on different production batches of detection chips, analysis parameters corresponding to or matching different batches of detection chips need to be used in the process of obtaining analysis data by using the analyzer. According to the control method of the analyzer provided by the embodiments of the present disclosure, by ensuring that the analysis parameter used in analyzing the substance to be analyzed is the analysis parameter corresponding to or matching the detection chip being used, the possible adverse effects, caused by the difference in the material of the detection chip, on the process of obtaining the analysis data of the substance to be analyzed may be reduced or avoided. Thus, the accuracy and reliability of the obtained analysis data may be improved while the detection process is simple and convenient to operate by using the detection chip, thereby being helpful for the user to obtain accurate and reliable analysis results, and satisfying the requirements of the user to achieve self-detection and self-analysis of the substance to be analyzed.

For example, the detection chip of the embodiments of the present disclosure may be a chip which can achieve integration or basic integration of basic operation units such as sample preparation, biological and chemical reactions, separation and detection, or the like, and has a size of several square centimeters. For example, the detection chip may be a microfluidic chip. Therefore, the substance to be analyzed contained in the detection chip can complete different biological or chemical reaction processes in the detection chip. The analyzer may use detection methods such as laser induced fluorescence, mass spectrum, ultraviolet, chemiluminescence, or the like to detect the products, so as to obtain detection data, and the analyzer may use the analysis parameter to acquire the analysis data as required according to the detection data. For example, the analysis data may include information such as the content or concentration value of a specific component in the substance to be analyzed.

For example, in some embodiments of the present disclosure, the analysis parameter includes a calculation curve for acquiring the analysis data based on the detection data of the detection chip.

For example, taking the case where the detection chip is detected by using an optical method to obtain the concentration value of a specific component in the substance to be analyzed as an example, the analyzer performs optical detection on the detection chip to obtain the detection data. For example, the detection data may be such as an absorbance value of the substance to be analyzed, and the analysis parameter may be a standard curve reflecting the relationship between the concentration value and the absorbance value of the component in the substance to be analyzed. Therefore, after the absorbance value of the substance to be analyzed is obtained through optical detection on the detection chip, the absorbance value is brought into the standard curve, so that the concentration value of the component in the substance to be analyzed corresponding to the absorbance value is obtained through calculation.

For example, in the process of detecting the detection chip by using the optical method, the concentration values of different components in the substance to be analyzed may be detected and analyzed by light with different wavelengths, so that the concentration values of various components in the substance to be analyzed can be detected and analyzed simultaneously by light with different wavelengths, thereby shortening the time required for the detection process and reducing the detection cost. For example, taking the case where the substance to be analyzed is breast milk as an example, the concentration values of lactose, fat, calcium, protein, and other components in the breast milk can be detected at the same time, so as to facilitate monitoring the concentration values of different components in the breast milk at any time to determine whether the expected indices are achieved.

Figure 3:
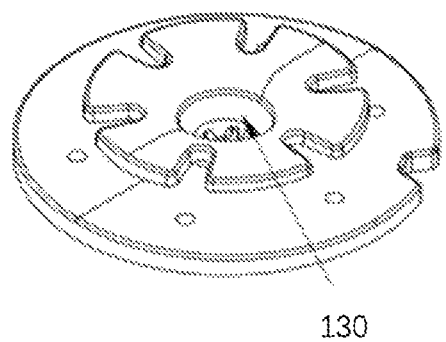
FIG. 3 is a schematic diagram of a detection chip provided by some embodiments of the present disclosure.
Figure 4A:
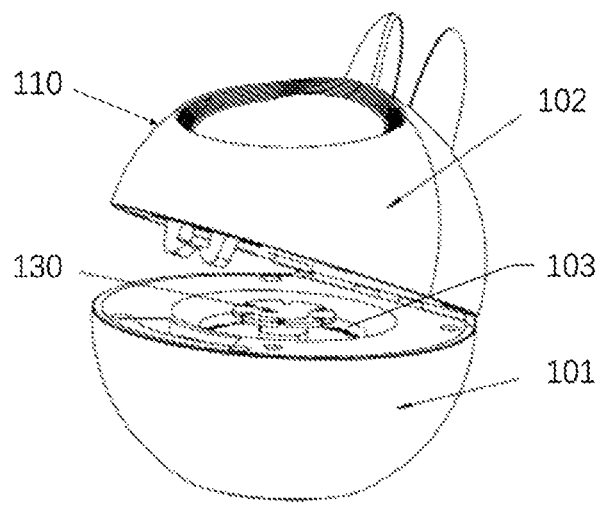
FIG. 4A to FIG. 4C are schematic diagrams of an analyzer provided by some embodiments of the present disclosure and detection with the analyzer on a detection chip.
Figure 4B:
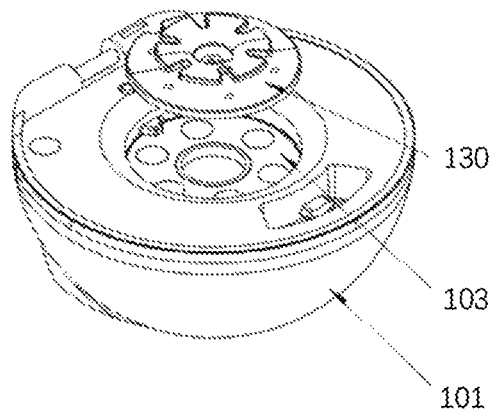
Figure 4C:
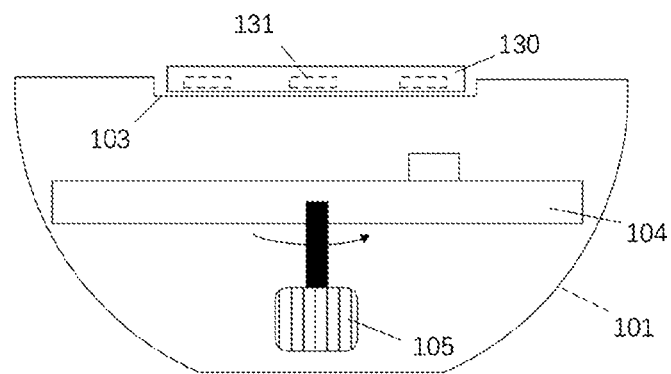

FIG. 3 is a schematic diagram of a detection chip provided by some embodiments of the present disclosure, and FIG. 4A to FIG. 4C are schematic diagrams of an analyzer provided by some embodiments of the present disclosure and detection with the analyzer on a detection chip. It should be noted that the embodiments of the present disclosure do not limit the type of detection chip, the appearance and mechanical structure of the analyzer, or the like, as long as the control method of the present disclosure can be applied.

For example, as illustrated in FIG. 3 to FIG. 4, the exemplary analyzer 110 includes a first housing 101, a second housing 102, and a chip placement structure 103. The chip placement structure 103 is located in the first housing 101 for placing the detection chip 130. For example, the detection chip 130 is a microfluidic detection chip, which includes at least one (for example, two or more) detection region. Upon the substance to be analyzed being injected into the detection chip, the substance to be analyzed flows into the at least one detection region through an injection port and a flow channel. The first housing 101 and the second housing 102 of the analyzer 110 can be turned on or turned off at one side, which is convenient for the user to place and retrieve the detection chip 130. Upon the analyzer 110 being used to perform detection on the detection chip 130 injected with the substance to be analyzed, the first housing 101 and the second housing 102 can avoid interference caused by external light.

For example, the analyzer 110 further includes a detection portion 104, and the detection portion 104 is provided in the first housing 101 and below the chip placement structure 103. For example, the detection chip 130 placed on the chip placement structure 103 can be detected through the detection portion 104, so as to obtain the analysis data of the substance to be analyzed contained in the detection chip 130.

During the using process, the first housing 101 and the second housing 102 may be opened first, the detection chip 130 can be placed on the chip placement structure 103, the substance to be analyzed can be injected into the detection chip 130, and then the first housing 101 and the second housing 102 may be closed, so that the analyzer 110 can detect the detection chip 130. After the detection is completed and the analysis data is obtained, the first housing 101 and the second housing 102 can be opened again, and the detection chip 130 can be taken out.

It should be noted that the structure of the detection chip 130 illustrated in FIG. 3 is only an example, and the embodiments of the present disclosure do not limit the specific structure of the detection chip 130.

For example, in the process of performing detection on the detection chip 130 including a plurality of detection regions 131 through the detection portion 104, the detection portion 104 can be rotated with the rotation driving device 105, so as to perform detection on different detection regions 131 of the detection chip 130. For example, the plurality of detection regions 131 may be used for detecting and analyzing the contents, concentration values, or the like of different components in the substance to be analyzed, so that simultaneous detection and analysis of the contents or concentration values of multiple components in the substance to be analyzed can be achieved by the analyzer 110.

For example, in the method illustrated in FIG. 1, after it is determined that the analyzer has obtained the analysis parameter corresponding to or matching the detection chip used for detection, the analyzer continues to perform a subsequent detection operation on the detection chip to obtain the analysis data. In another aspect, in the case of being determined that the analyzer does not obtain the analysis parameter, the analyzer sends out a request for obtaining the analysis parameter, and the analyzer then continues to perform the subsequent detection operation after ensuring that the analysis parameter is obtained. Therefore, it can ensure that the analyzer analyzes the substance to be analyzed by using the analysis parameter matched with the detection chip being used, thereby improving the accuracy and reliability of the obtained analysis data and helping the user to obtain accurate and reliable analysis results.

For example, in some embodiments of the present disclosure, obtaining the analysis parameter includes: allowing the analyzer to be in signal connection with a parameter storage device storing the analysis parameter through the communication interface, and reading and storing the analysis parameter, so that the analyzer can obtain the analysis data matched with the detection chip.

Figure 2:
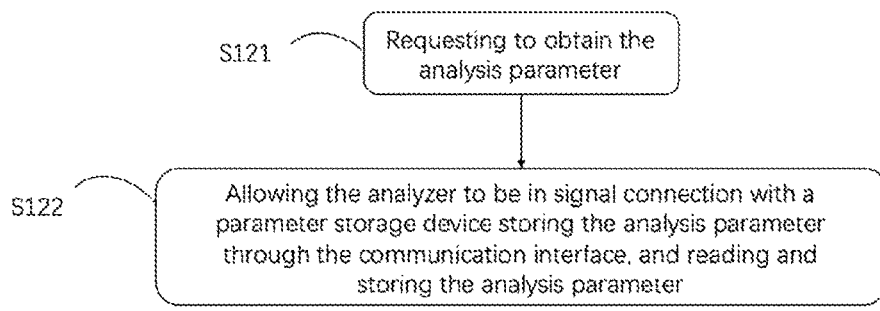
FIG. 2 is a flowchart of a specific example of Step S120 illustrated in FIG. 1.

FIG. 2 is a flowchart of a specific example of Step S120 illustrated in FIG. 1.

For example, as illustrated in FIG. 2, in the case of being determined that the analyzer does not obtain the analysis parameter corresponding to the detection chip used for detection, Step S120 may include the following steps S121 and S122.

Step S121: requesting to obtain the analysis parameter.

For example, the analyzer may send out a request for obtaining the analysis parameter by displaying an image, making a sound, vibrating, or other methods. Alternatively, the analyzer may also send out the request for obtaining the analysis parameter through other devices, such as being in signal connection with the analyzer, by displaying an image, making a sound, vibrating, or other methods, and the embodiments of the present disclosure are not limited in this aspect.

Step S122: allowing the analyzer to be in signal connection with a parameter storage device storing the analysis parameter through the communication interface, and reading and storing the analysis parameter.

For example, the analyzer includes a communication interface. According to the type of communication interface, the analyzer and the parameter storage device can be directly connected through the communication interface to achieve signal connection, or can also be connected through connection media such as a data line, a signal line, or the like to achieve signal connection, or the signal connection between the analyzer and the parameter storage device can also adopt wireless communication connection or other suitable signal connection methods, and the embodiments of the present disclosure are not limited in this aspect. The communication interface is a part of a communication device, and the communication device may be dedicated to communication with the parameter storage device, and may also be reused for communication for other purposes.

Figure 5:
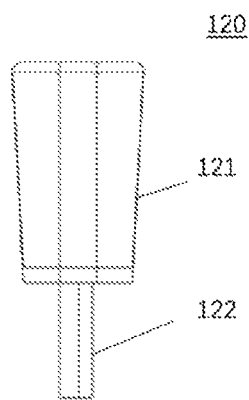
FIG. 5 is a schematic diagram of a parameter storage device provided by some embodiments of the present disclosure.
Figure 6:
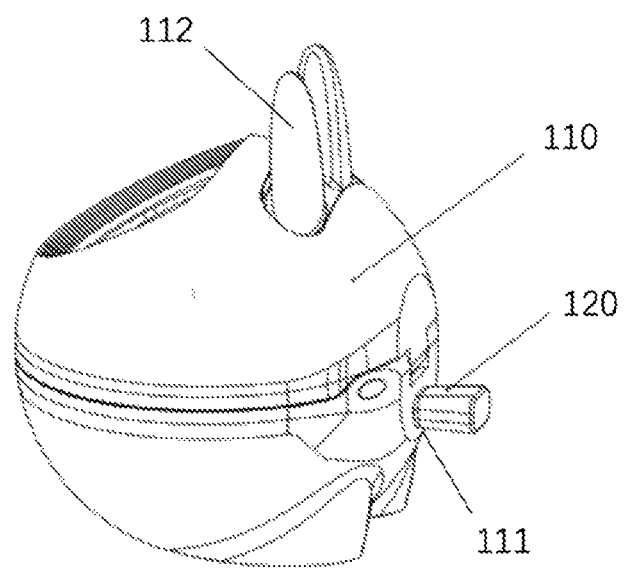
FIG. 6 is a schematic diagram of a signal connection method between an analyzer and a parameter storage device provided by some embodiments of the present disclosure.

FIG. 5 is a schematic diagram of a parameter storage device provided by some embodiments of the present disclosure, and FIG. 6 is a schematic diagram of a signal connection method between an analyzer and a parameter storage device provided by some embodiments of the present disclosure.

For example, as illustrated in FIG. 5 and FIG. 6, the parameter storage device 120 may be a USB flash drive, the communication interface 111 of the analyzer 110 is a USB interface, and the analyzer 110 correspondingly includes a USB control device as the communication device. Therefore, by directly inserting the data interface 122 of the parameter storage device 120 into the communication interface 111 provided on the surface of the analyzer 110, the signal connection between the analyzer 110 and the parameter storage device 120 can be achieved, so as to allow the analyzer 110 to read and store the analysis parameter stored in the parameter storage device 120.

For example, as illustrated in FIG. 5, the parameter storage device 120 includes a housing 121 and further includes a control circuit, a memory (not shown), or the like provided in the housing 121. The analysis parameter is stored in the memory. The control circuit is configured to establish the signal connection between the parameter storage device 120 and the analyzer 110, and is further configured to read the analysis parameter from the memory, so as to transmit the read analysis parameter to the analyzer 110 through the communication interface 111 upon the parameter storage device 120 being in signal connection with the analyzer 110. For example, the control circuit includes a processor.

For example, a material of the housing 121 may be thermoplastic elastomer (TPE) or other suitable materials, such as a material that can protect the control circuit, memory, or the like provided in the housing 121, and the embodiments of the present disclosure are not limited in this aspect.

For example, in some embodiments of the present disclosure, the communication interface 111 of the analyzer 110 illustrated in FIG. 6 is further configured to charge the analyzer 110. Therefore, the communication interface 111 can provide various functions such as charging, data reading and writing, etc., and improve the utilization rate of the communication interface 111, thereby improving the overall operation performance of the analyzer 110 and improving the user experience. At the same time, because the communication interface 111 is usually provided on the surface of the analyzer 110, the communication interface 111 with multiple functions may also facilitate optimizing the design of the analyzer 110, thereby further improving the user experience. As mentioned above, for example, the communication interface 111 is a USB interface, which may be of the Type-A, Type-B, Type-C, etc. Therefore, the communication interface 111 can have both the communication function and the charging function. The embodiments of the present disclosure are not limited thereto, and the above-mentioned communication interface may also be a lighting interface, etc.

It should be noted that, in some other embodiments of the present disclosure, the analyzer 110 may use, for example, a battery built in the analyzer 110 for power supply. In other embodiments, the analyzer 110 may also be electrically connected to an external power supply by using a wire for power supply. For example, the external power supply may be a transformer, so as to convert the daily electricity (e.g., 220V or 110V) into the voltage type (e.g., direct current) and the voltage (e.g., 5V or 12.5V) required by the analyzer, thereby omitting the charging process of the analyzer 110 for convenience of the user. The embodiments of the present disclosure are not limited thereto.

It should be noted that, in the process of performing detection on the detection chip by using the analyzer 110, the analyzer 110 can be opened and the detection chip can be placed on a supporting table (for example, the chip placement structure 103) inside the analyzer 110, so as to achieve the detection and analysis of the substance to be analyzed contained in the detection chip.

It should be noted that, in the embodiments of the present disclosure, the signal connection method between the analyzer and the parameter storage device, the type of the parameter storage device, etc. include but are not limited to the above situations.

For example, according to the communication interfaces of different types of analyzers, the above-mentioned parameter storage device may also be a storage device such as a hard disk, a floppy disk, a magneto-optical disk, etc.; or, the above-mentioned parameter storage device may also be an electronic device with a storage function, such as a mobile phone, a computer, etc., and may be in signal connection with the communication interface of the analyzer through such as a signal line, a data line, or the like. The embodiments of the present disclosure are not limited thereto.

For example, in some embodiments of the present disclosure, the communication interface of the analyzer may also be a wireless communication interface, and accordingly, the parameter storage device may be a first mobile terminal. For example, the wireless communication interface may include the mobile hotspot (WiFi), Bluetooth, near field communication (NFC), mobile communication (such as 2G/3G/4G/5G), etc. The first mobile terminal may be a mobile terminal with a wireless communication function, such as a mobile phone, a computer, or the like, and may also be an IC card (such as a contactless IC card). Therefore, the signal connection between the analyzer and the parameter storage device is achieved by wireless communication, so that the analyzer and the parameter storage device can move relatively flexibly with each other, thereby providing convenience for the user to operate, carry, etc.

Figure 7:
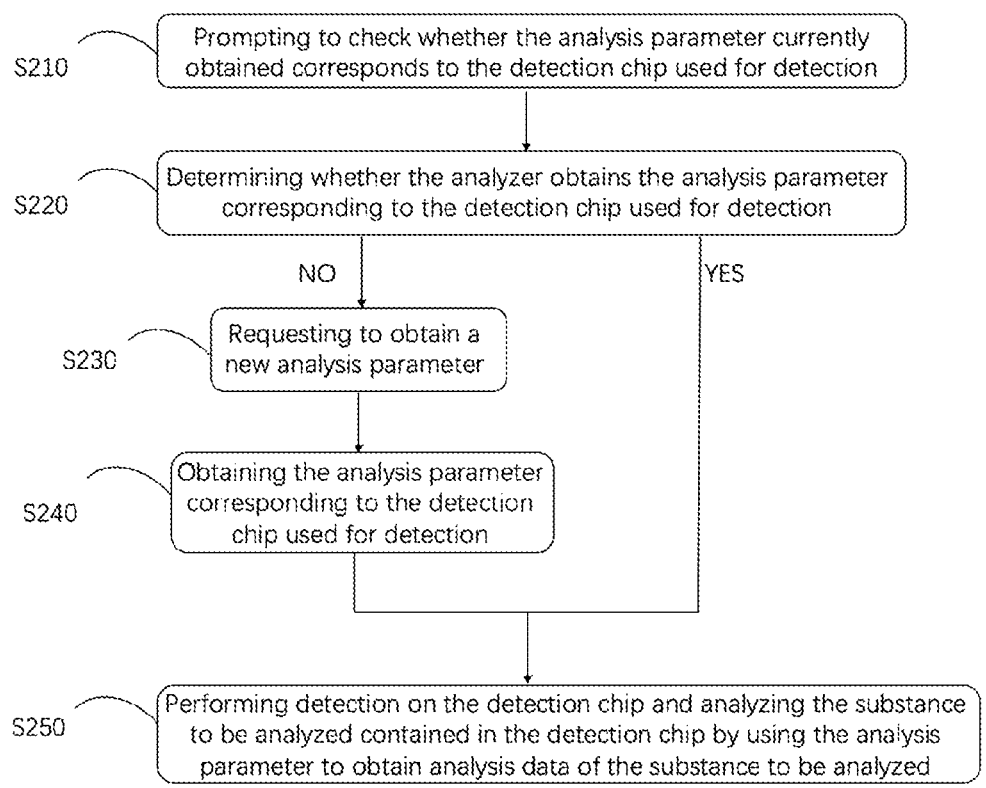
FIG. 7 is a flowchart of another control method of an analyzer provided by some embodiments of the present disclosure.

FIG. 7 is a flowchart of another control method of an analyzer provided by some embodiments of the present disclosure. For example, as illustrated in FIG. 7, the method includes the following steps S210-S250.

Step S210: prompting to check whether the analysis parameter currently obtained corresponds to the detection chip used for detection.

For example, after the analyzer is turned on and completes self-inspection, upon detecting that the analysis parameter is stored in the analyzer, the analyzer sends out a check prompt to the user by displaying an image, making a sound, or other methods, or the analyzer may also send out the check prompt to the user through other devices, such as being in signal connection with the analyzer, by displaying an image, making a sound, or other methods. For example, the analyzer displays an identification code (for example, including a number or a letter) corresponding to the analysis parameter for the user to check, and the embodiments of the present disclosure are not limited in this aspect.

Step S220: determining whether the analyzer obtains the analysis parameter corresponding to the detection chip used for detection.

For example, after receiving the prompt in Step S210, the user checks whether the analysis parameter currently obtained by the analyzer corresponds to the analysis parameter of the detection chip to be used for the current detection, and provides a check result to the analyzer or such as a mobile terminal in signal connection with the analyzer, so that the analyzer can determine whether the analysis parameter corresponding to the detection chip used for the detection is obtained. For example, an identification code corresponding to the analysis parameter is printed on an outer packaging or a surface of the detection chip to be used for the comparison by the user.

For example, the user can directly press or dial a corresponding button or switch provided on the analyzer to provide a verification result, and the analyzer generates a control signal to perform a corresponding operation according to the received verification result. For example, the analyzer may also be in signal connection with a mobile terminal with a remote control function, such as an infrared remote controller or the like. After the user provides the verification result to the mobile terminal, the mobile terminal generates a corresponding control signal and transmits the control signal to the analyzer, so that the analyzer can perform a corresponding operation according to the control signal. For example, the user may feed back the verification result by pressing a button on the infrared remote controller. For example, according to the actual structure and functional design of the analyzer, the user may also provide the verification result through the touch screen or other input devices on the analyzer or mobile terminal, or may also provide the verification result by voice through an audio device of the analyzer or mobile terminal. In the embodiments of the present disclosure, an applicable method of obtaining the verification result may be selected according to the structure, function, or the like of the analyzer and associated equipment, and the embodiments of the present disclosure are not limited in this aspect.

For example, upon checking whether the analysis parameter currently obtained corresponds to the detection chip used for detection, the user may check whether the parameter storage device storing the analysis parameter matches with the detection chip. For example, it can be checked whether the identification codes provided on the detection chip and the parameter storage device correspond to each other. For example, it can be checked whether the same set of codes are printed on the detection chip and the parameter storage device. Alternatively, for example, the equipment with a scanning function may be used to scan the identifications such as bar codes or two-dimensional codes on the detection chip and the parameter storage device for verification. Alternatively, in the case where the parameter storage device has a display function, it may also be checked by looking up the display information provided by the parameter storage device, and the embodiments of the present disclosure are not limited thereto.

For example, because the analysis parameter stored in the parameter storage device needs to be matched with the detection chip, the parameter storage device may be batch-bound with the corresponding detection chip at the time of delivery, so that the parameter storage devices of different batches cannot be used universally, thereby ensuring that the analysis parameter used for detecting and analyzing the substance to be analyzed corresponds to the detection chip being used. For example, for the convenience of the user, the detection chip and the corresponding parameter storage device may be placed in the same packaging box for the user.

Step S230: requesting to obtain a new analysis parameter in a case where the analysis parameter currently obtained does not correspond to the detection chip used for detection.

Step S240: obtaining the analysis parameter corresponding to the detection chip used for detection.

Step S250: performing detection on the detection chip and analyzing the substance to be analyzed contained in the detection chip by using the analysis parameter to obtain analysis data of the substance to be analyzed.

For example, as illustrated in FIG. 7, in the case where it is determined that the analyzer has obtained the analysis parameter corresponding to the detection chip used for detection by checking that the analysis parameter currently obtained corresponds to the detection chip used for detection, the operation of Step S250 is directly performed after Step S220. In the case where it is determined that the analysis parameter currently obtained does not correspond to the detection chip used for detection after checking, and then it is determined that the analyzer does not obtain the analysis parameter corresponding to the detection chip used for detection, the operation of Step S230 is performed after Step S220.

In the above exemplary method, Step 210 does not need to be performed before Step S220, but may also be performed after Step 220, that is, the analyzer may either perform the self-inspection after starting up and then detect whether the analysis parameter is obtained, or perform the self-inspection after detecting whether the analysis parameter is obtained.

It should be noted that, the specific contents of Step S230 and Step S240 may refer to the descriptions of Step S121 and Step S122 in FIG. 2, respectively, the specific contents of Step S250 may refer to the descriptions of Step S130 in FIG. 1, and repeated contents are omitted herein.

For example, in some embodiments of the present disclosure, the analyzer further includes at least one micro switch, and the control method of the analyzer provided by the embodiments of the present disclosure further includes: detecting an operation applied to the micro switch, and generating a control signal according to the operation. The control signal is used for an interaction process of the analyzer For example, a control signal may be provided to the analyzer by controlling such as the switch state, rotation angle, or touch sensing of the micro switch, so that the analyzer can execute corresponding operation steps according to the control signal, thereby achieving the interaction process between the analyzer and the user or other equipment, and further achieving the control of the analyzer through the interactive operation.

For example, taking the control method of the analyzer illustrated in FIG. 7 as an example, after checking whether the analysis parameter currently obtained corresponds to the detection chip used for detection, the user may provide a control signal to the analyzer by operating the micro switch, so that the analyzer can determine whether the analyzer has obtained the analysis parameter corresponding to the detection chip used for detection according to the control signal, so as to select the subsequent step to be performed.

In some other embodiments of the present disclosure, in addition to controlling the micro switch, the control signal may also be provided to the analyzer in other ways, so as to achieve the interaction process between the analyzer and the user or other equipment, and the embodiments of the present disclosure are not limited in this aspect. For example, the control signal used for the interaction process of the analyzer may also be generated and provided by a mobile terminal being in signal connection with the analyzer and with a remote control function, so as to achieve the interaction process between the analyzer and the mobile terminal, or achieve the interaction process between the analyzer and the user through the mobile terminal, and the embodiments of the present disclosure are not limited in this aspect.

For example, in some embodiments of the present disclosure, the micro switch may be the micro switch 112 of the analyzer 110 as illustrated in FIG. 6. For example, as illustrated in FIG. 6, the micro switch 112 protrudes outwards from a surface of the analyzer 110 and has a long strip shape, and the micro switch 112 is configured to be capable of being operated in at least two directions. For example, the micro switch 112 may be operated in multiple directions, such as an up-down direction, a left-right direction, or the like, and may even be operated in both the up-down direction and the left-right direction, and the embodiments of the present disclosure are not limited in this aspect.

For example, the micro switch 112 may has a strip shape similar to the rabbit-ear shape illustrated in FIG. 6, which is convenient for the user to operate the micro switch 112, and facilitates the optimization of the design of the analyzer 110, thereby improving the user experience.

For example, the number of micro switches of the analyzer may be two as illustrated in FIG. 6, or may also be one, three, four or more, etc. For example, the micro switch in the analyzer may be provided at an upper part of the analyzer as illustrated in FIG. 6, or may also be provided at other suitable positions on the analyzer, and the embodiments of the present disclosure are not limited in this aspect.

For example, in some embodiments of the present disclosure, generating the control signal according to the operation applied to the micro switch includes: generating different control signals for interaction according to operations of the micro switch in different directions. Therefore, the analyzer can achieve different interactive functions through different control signals generated based on the operations applied to the micro switch, thereby achieving flexible control of the analyzer through cross operation, improving the operating performance of the analyzer, and optimizing the user experience of the analyzer.

For example, taking the analyzer 110 in the above embodiments as an example, the micro switch 112 can be operated in different directions, such as the up-down direction, left-right direction, etc., to provide, for example, a control signal for determining whether the analyzer obtains the analysis parameter corresponding to the detection chip used for detection, a control signal for switching the working state of the analyzer 110 (for example, a control signal for turning on or turning off the analyzer 110, allowing the analyzer 110 to enter a sleep state, etc.), or other suitable control signals used for interaction. The embodiments of the present disclosure are not limited in this aspect.

For example, in some embodiments of the present disclosure, the analyzer further includes a display device, and the control method of the analyzer provided by some embodiments of the present disclosure further includes: displaying the analysis data through the display device, or allowing the display device to display different interactive operation interfaces according to the control signal.

For example, the display device may display the above-mentioned analysis data, so that the user can intuitively obtain the analysis data through the display device. Alternatively, the display device may be used to provide a display image corresponding to Step S210 in FIG. 7 described above, or may display an interactive operation interface corresponding to Step S230 in FIG. 7 described above according to the control signal, and the embodiments of the present disclosure are not limited in this aspect.

For example, the display device may be any product or component with a display function, such as an LCD display device, an OLED display device, a QLED display device, an electronic paper display device, etc., and the embodiments of the present disclosure are not limited in this aspect. In addition, the display device may also have such as a touch function, so as to facilitate the user to operate and view the operation process.

For example, in some embodiments of the present disclosure, the analysis data obtained by the analyzer includes a plurality of items (for example, a plurality of components or different parameters of each component), and displaying the analysis data through the display device described above includes: switching a display page of the display device according to the control signal so as to display different items in the analysis data. Therefore, in the case where the analysis data includes a plurality of items, the analyzer may flexibly display the plurality of items on different pages through the display device, for example, the display pages providing different items may be sequentially displayed according to the control signal, or the display page including a specific item may be displayed according to the control signal, and the embodiments of the present disclosure are not limited in this aspect.

For example, in some embodiments of the present disclosure, the analyzer further includes a communication device, and the control method of the analyzer provided by the embodiments of the present disclosure further includes: allowing the analyzer to be in signal connection with a second mobile terminal through the communication device, and receiving the control signal provided by the second mobile terminal or providing the analysis data to the second mobile terminal.

For example, the second mobile terminal may be a device with a communication function, such as a mobile phone, a computer, a server, a remote controller, etc. For example, the signal connection between the second mobile terminal and the analyzer may be wired communication connection implemented through a signal line, a data line, etc., and may also be wireless communication connection using such as the mobile hotspot (WiFi), Bluetooth, near field communication (NFC), mobile communication (such as 2G/3G/4G/5G), etc. For example, the second mobile terminal may be implemented as the same terminal device as the above-mentioned first mobile terminal, or may also be provided separately, and the embodiments of the present disclosure are not limited in this aspect.

Because the analyzer includes the communication device connected with the second mobile terminal, the analyzer may provide different operation modes, including an online mode and an offline mode. The online mode allows the analyzer to be connected with a mobile terminal such as a mobile phone, a computer (such as a tablet computer), or the like, so as to interact with the user depending on the mobile terminal, and upload detection and analysis data to the mobile terminal. The offline mode allows the analyzer to independently interact with the user and provide detection and analysis results without being connected to the mobile terminal.

For example, the communication device may be such as a USB interface or the like, so as to achieve the signal connection between the analyzer and the second mobile terminal through wired communication connection, or the communication device may also be the above-mentioned wireless communication interface such as the mobile hotspot (WiFi), Bluetooth, near field communication (NFC), mobile communication (such as 2G/3G/4G/5G), etc., and the embodiments of the present disclosure are not limited in this aspect.

For example, in the case where the analyzer receives the control signal provided by the second mobile terminal through the communication device, the second mobile terminal may apply the control signal to the analyzer through signal connection, so as to control the analyzer to achieve different interactive functions, control the display image provided by the display device of the analyzer, etc., so that the analyzer can be controlled through interactive operations.

For example, in the case where the analyzer provides the analysis data to the second mobile terminal, the second mobile terminal may be a mobile device with a storage function. After receiving the analysis data, for example, the mobile device stores the analysis data in a memory for subsequent use, or the mobile device transmits the analysis data to another device which is difficult to achieve direct signal connection with the analyzer, thereby achieving sharing or real-time uploading of the analysis data. For example, the second mobile terminal may also be a mobile device with a display function, so that the analysis data may also be displayed on the second mobile terminal.

For example, in some embodiments of the present disclosure, the control method of the analyzer further includes: determining whether to establish the signal connection between the analyzer and the second mobile terminal through the communication device, and selecting an operation mode. For example, the analyzer determines whether to establish the signal connection between the analyzer and the second mobile terminal through the communication device, and prompts the user to select the offline mode in the case of being determined that the analyzer is not connected to the second mobile terminal, or prompts the user to re-select (switch) the operation mode in the case that the user has selected the online mode.

For example, in some embodiments of the present disclosure, the second mobile terminal has a display function, and the control method of the analyzer further includes: displaying the analysis data and/or an analysis result provided based on the analysis data through the second mobile terminal, or displaying an interactive operation interface through the second mobile terminal for generating the control signal.

For example, the second mobile terminal may be configured to have a relatively large display screen, so as to provide a more impeccable display image compared with the analyzer, so that the user can intuitively obtain more complete and abundant information related to the analysis data through the second mobile terminal. For example, in the case of the analysis data including a plurality of items, the plurality of items may be displayed simultaneously through the display screen of the second mobile terminal, so that the user can obtain the required analysis data more intuitively through the second mobile terminal, thereby improving the user experience. For example, the second mobile terminal may also provide the analysis result based on the analysis data in the display page providing the analysis data, so that the user can obtain more information related to the analysis data at the same time.

For example, in the case of the analysis data and the analysis result provided based on the analysis data being displayed through the second mobile terminal, taking the case where the substance to be analyzed is breast milk as an example, the analysis data may be the content or concentration value of one or more components in the breast milk, and the analysis result may be professional nutrition matching, dietary guidance, clinical advice, etc., provided based on the substance content analysis of the breast milk. For example, the analysis result may be directly given by such as an application program (APP) installed on the second mobile terminal, or the analysis result may be obtained by uploading the analysis data to a server through the second mobile terminal and searching and querying through the server, and the embodiments of the present disclosure are not limited in this aspect.

For example, in the case of the interactive operation interface being displayed by the second mobile terminal for generating the control signal, the interactive operation interface displayed by the second mobile terminal may be a prompt page or a request page that is sent to the user, such as the interactive operation pages corresponding to Step S210 and Step S230 in FIG. 7, so that the user may perform corresponding operations according to the display information provided by the second mobile terminal, and the analyzer or equipment being in signal connection with the analyzer can generate the corresponding control signal based on the applied operation, thereby achieving the control of the analyzer through the interactive operation.

Figure 8:
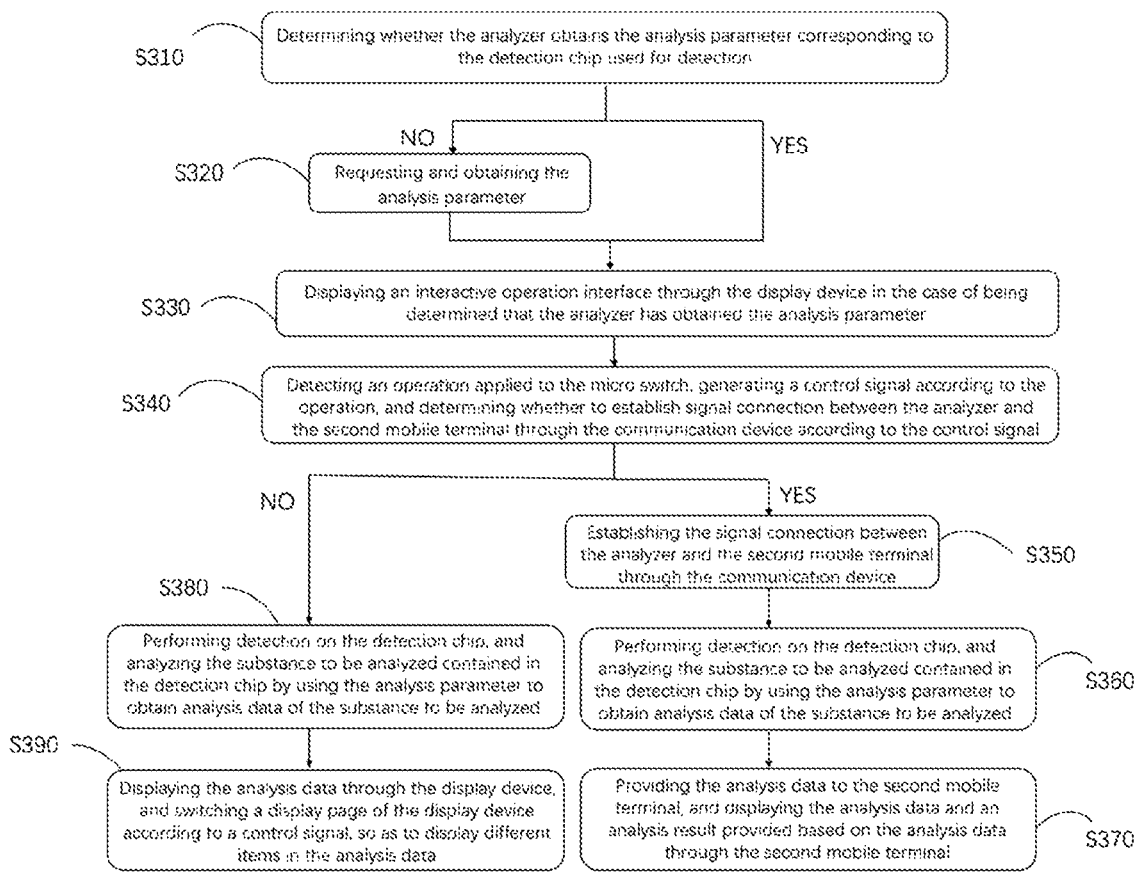
FIG. 8 is a flowchart of still another control method of an analyzer provided by some embodiments of the present disclosure.

FIG. 8 is a flowchart of still another control method of an analyzer provided by some embodiments of the present disclosure. For example, as illustrated in FIG. 8, the method includes the following steps.

Step S310: determining whether the analyzer obtains the analysis parameter corresponding to the detection chip used for detection.

Step S320: requesting and obtaining the analysis parameter in the case of being determined that the analyzer does not obtain the analysis parameter.

Step S330: displaying an interactive operation interface through the display device in the case of being determined that the analyzer has obtained the analysis parameter.

Step S340: detecting an operation applied to the micro switch, generating a control signal according to the operation, and determining whether to establish signal connection between the analyzer and the second mobile terminal through the communication device according to the control signal.

Step S350: establishing the signal connection between the analyzer and the second mobile terminal through the communication device in the case of being determined to establish the signal connection between the analyzer and the second mobile terminal through the communication device.

Step S360: performing detection on the detection chip, and analyzing the substance to be analyzed contained in the detection chip by using the analysis parameter to obtain analysis data of the substance to be analyzed.

Step S370: providing the analysis data to the second mobile terminal, and displaying the analysis data and an analysis result provided based on the analysis data through the second mobile terminal.

Step S380: in the case where the analyzer is not in signal connection with the second mobile terminal through the communication device, performing detection on the detection chip, and analyzing the substance to be analyzed contained in the detection chip by using the analysis parameter to obtain analysis data of the substance to be analyzed.

Step S390: displaying the analysis data through the display device, and switching a display page of the display device according to a control signal, so as to display different items in the analysis data.

For example, in some embodiments of the present disclosure, the control method of the analyzer further includes: performing equipment detection on the analyzer to determine whether the analyzer satisfies a condition for performing detection on the detection chip.

For example, the analyzer first performs self-inspection after starting up to determine whether the analyzer meets the conditions for performing detection on the detection chip, and in the case of being determined that the analyzer meets the conditions for performing detection on the detection chip, the analyzer will perform subsequent detection and analysis operations. For example, in the case of being determined that the analyzer meets the conditions for performing detection on the detection chip, the corresponding method illustrated in FIG. 1, FIG. 7 or FIG. 8 is continued to be executed to achieve the control of the analyzer. In the case where the analyzer does not meet the conditions for performing detection on the detection chip, prompt warning is given and the analyzer is requested to be tested or repaired, so that the analyzer can meet the conditions for performing detection on the detection chip. Therefore, the analyzer can be ensured to be in a normal and stable working state upon the analyzer being used for performing detection on the detection chip, thereby ensuring the accuracy and reliability of the obtained analysis data.

For example, the equipment detection performed on the analyzer includes detection of detecting the light path of the analyzer, detection of the environment temperature, humidity, and other conditions, etc.

For example, in some embodiments of the present disclosure, the substance to be analyzed includes a breast milk sample. For example, by using the control method of the analyzer provided by the embodiments of the present disclosure, accurate and convenient detection and analysis of the breast milk can be achieved, thereby obtaining accurate contents of various components in the breast milk. Therefore, the user can complete the detection and analysis process of the breast milk sample on the user's own through the control method of the analyzer provided by the embodiments of the present disclosure, and can accurately and quickly obtain the content of each component in the breast milk. For example, the user can further acquire such as dietary guidance, nutrition matching suggestions, or the like provided based on the content of each component in the breast milk, thereby improving the user experience.

Hereinafter, with reference to the analyzer 110 and the parameter storage device 120 illustrated in FIG. 6, the case where the analyzer is used for detecting and analyzing breast milk and the second mobile terminal is a mobile phone is taken as an example to describe a specific example of the control method of the analyzer provided by some embodiments of the present disclosure.

For example, upon the analyzer being used to detect and analyze breast milk for the first time, the analyzer can be started by short pressing one micro switch of the analyzer. For example, the micro switch may be a switch having a rabbit-ear shape on the right side of the user upon watching the display screen of the analyzer, such as the micro switch 112 illustrated in FIG. 6. In order to distinguish the plurality of micro switches on the analyzer, the micro switch is hereinafter referred to as the first switch. After the first switch is pressed by the user for short time, the analyzer starts and is in a working state. If the first switch is pressed by the user for long time, the analyzer will shut down.

After the analyzer is started, the above steps of equipment detection are performed on the analyzer to determine whether the analyzer meets the conditions for performing detection on the detection chip. For example, the equipment detection process can be completed by the analyzer under the control of the control device inside the analyzer. For example, the analyzer detects the detecting light path of the analyzer, the detection environment temperature, humidity and other conditions, or the like according to the control signal generated by the control device. In the case that the analyzer does not meet the conditions for performing detection on the detection chip, the control device generates a corresponding control signal, so that the analyzer may send a prompt warning to the user and request the analyzer to be tested or repaired. In the case where it is determined that the analyzer meets the conditions for performing detection on the detection chip, the equipment detection process ends, and the display device (e.g. display screen) of the analyzer displays the equipment name of the analyzer, such as "breast milk analyzer," according to the control signal of the control device.

According to the control signal sent by the control device, the analyzer automatically detects whether it is used for the first time. If the analyzer is determined to be powered on for the first time, a request for acquiring the analysis parameter is sent to the user through the display screen, for example, the analyzer prompts such as "Please insert the parameter storage device" or "Please connect the parameter storage device" may be displayed to the user through the display screen. For example, the parameter storage device may be the parameter storage device 120 illustrated in FIG. 5. After receiving the request sent by the analyzer, the user inserts the parameter storage device 120 into the communication interface 111 of the analyzer 110 as illustrated in FIG. 6, so that the parameter storage device 120 is in signal connection with the analyzer 110. For example, the communication interface 111 is a B-type USB interface, which can be used for reading and writing data and charging the analyzer 110.

After the analyzer is in signal connection with the parameter storage device, the analyzer automatically identifies and reads the corresponding analysis parameter from the parameter storage device, for example, the analysis parameter may be a standard curve reflecting the relationship between the concentration values and the absorbance values of a component in the substance to be analyzed. After the analyzer reads and stores the analysis parameter, the algorithm for calculating the analysis data stored in the memory of the control device will be automatically updated to ensure the accuracy and reliability of the analysis data obtained by using the analyzer. After it is determined that the analyzer has obtained the analysis parameter corresponding to the detection chip used for detection, the display screen displays "Analysis parameter has been updated," and after a short stay, the interface of breast milk selection stage is displayed, that is, the subsequent breast milk selection operation stage is entered.

If it is determined that the analyzer is not powered on for the first time after self-inspection, the user will be promoted to check whether the analysis parameter currently obtained corresponds to the detection chip used for detection through the display screen, for example, "Please check detection parameter" will be displayed through the display screen. After checking that the code on the parameter storage device or the code displayed on the display screen is consistent with the code on the detection chip and operating to determine that the analysis parameter currently obtained corresponds to the detection chip used for detection, the user short presses the first switch. After detecting the operation that the user short presses the first switch, the control device of the analyzer generates a control signal to allow the analyzer to jump to a detection selection mode, for example, the user can select the "online" mode or the "offline" mode through the display screen.

For example, the user can select the mode (e.g., move the cursor on the display screen) by short pressing the left-ear switch (e.g., the micro switch adjacent to the micro switch 112 illustrated in FIG. 6) adjacent to the first switch, and confirm by short pressing the first switch. After detecting the user's short pressing of the first switch, the control device of the analyzer generates a control signal according to the operation, and determines whether to establish signal connection between the analyzer and the mobile terminal such as a mobile phone according to the control signal, thereby achieving the interactive operation between the user and the analyzer. For example, the display screen displays two choices: "offline use" (i.e., an offline mode) or "APP use" (i.e., an online mode).

If the user selects the "offline use", the analyzer will enter the breast milk selection operation stage according to the generated control signal. If the user selects the "APP use," the signal connection between the analyzer and the mobile phone is established through the communication device of the analyzer. In this case, the user needs to open the corresponding APP on the mobile phone, and open the Bluetooth equipment to select the analyzer, or open the WIFI to select the analyzer through an intelligent gateway, so as to establish the signal connection between the mobile phone and the analyzer. If the signal connection between the mobile phone and the analyzer is successfully established, the mobile phone displays that the connection is successful, and the analyzer enters the breast milk selection operation stage according to the generated control signal. If the signal connection between the mobile phone and the analyzer fails, the mobile phone displays that the connection is failed, prompts the user to try the signal connection again, and provides the user with possible reasons for the signal connection failure. If the signal connection between the mobile phone and the analyzer fails for many times, the analyzer allows the user to select, through the display screen, whether to short press the first switch to select the "offline use" mode, that is, whether to choose not to establish the signal connection between the analyzer and the mobile phone. If the user selects the "offline use" mode, the analyzer will enter the breast milk selection operation stage according to the generated control signal.

In the breast milk selection operation stage, the user selects a stage where the substance to be analyzed (i.e., breast milk) belongs. For example, stages include: "colostrum (0-4 days), transitional milk (5-14 days), and mature milk (after 14 days)." In the "offline use" mode, the above stages are displayed on the display screen of the analyzer, and the user can select the breast milk stage through the left-ear switch and confirm the breast milk stage selection by short pressing the right-ear switch. The analyzer enters the breast milk detection stage according to the generated control signal. In the "APP use" mode, the above stages are displayed on the screen of the mobile phone through the APP of the mobile phone, the user can select on the mobile phone, and the analyzer enters the breast milk detection stage after receiving the control signal generated by the mobile phone.

In the breast milk detection stage, "Please open the cover and put in the chip to start detection" is displayed on the display screen of the analyzer. The user can put the detection chip into the analyzer according to the operating instructions, drip the breast milk into the detection chip, and close the upper cover of the analyzer. In the "APP use" mode, "Please open the cover and put in the chip to start detection" will be displayed synchronously on the screen of the mobile phone, and more detailed legend operation steps will be provided at the same time, which is convenient for the user to operate. The analyzer generates a control signal according to the operation of closing the upper cover of the analyzer. After determining that the detection chip has been placed in the correct position, the breast milk has been dripped into the detection chip sufficiently, and the detection chip has been filled with liquid, the breast milk is detected and analyzed based on the analysis parameter to acquire the analysis data of the breast milk.

After the breast milk is detected and analyzed, the obtained analysis data is played on the display screen of the analyzer. For example, the analysis data may include six indicators, which are automatically displayed in turn on the display screen, and each indicator is displayed on the display screen for about 3 seconds. In the process of displaying the analysis data, the user can short press the first switch to switch the automatic carousel mode to a manual page turning mode to view the six indicators. After the six indicators are displayed in turn on the display screen for one time, a downloaded QR code of a mobile APP may be displayed on the display screen, so that the user can acquire the mobile APP by scanning the downloaded QR code. After the downloaded QR code stays on the display screen for a short time, the interactive operation interface of "detect again" and "view the result again" may be displayed on the display screen. The user can select through the left-ear switch and short press the right-ear switch for confirmation. If the user selects "detect again," the analyzer jumps the display page to the interface of the breast milk selection stage interface according to the control signal. If the user selects "view the result again," the analyzer jumps the display page to the page that six indicators are displayed in turn according to the control signal. At this point, all interactive processes of detecting and analyzing the breast milk with the analyzer are completed.

In the "APP use" mode, the analysis data, such as the above-mentioned six indicators, and the analysis result based on the analysis data, such as recommended recipes, diet nursed back to health, etc., may be displayed on the screen of the mobile phone, so that the user can obtain more information related to the analysis data and understand the analysis data more intuitively.

At least one embodiment of the present disclosure further provides an analyzer, and the analyzer includes a detection portion and a control device. The detection portion is configured to perform detection on a detection chip and receive detection data of the detection chip. The control device is configured to determine whether an analysis parameter corresponding to the detection chip used for detection is obtained and request to obtain the analysis parameter in a case where the analysis parameter is not obtained, and the control device is further configured to, in a case of being determined that the analysis parameter is obtained, allow the detection portion to perform detection on the detection chip to obtain the detection data, and analyze the detection data by using the analysis parameter to obtain analysis data of a substance to be analyzed contained in the detection chip.

The analyzer provided by the embodiments of the present disclosure can reduce or avoid the possible adverse effects of the difference in the material of the detection chip on the obtained analysis data of the substance to be analyzed by ensuring that the analysis parameter being used is the analysis parameter corresponding to or matched with the detection chip being used in the case of analyzing the substance to be analyzed, thereby improving the accuracy and reliability of the obtained analysis data while achieving the simple and convenient operation of the detection process by using the detection chip, so as to help the user to acquire accurate and reliable analysis results and meet the requirements of the user for self-inspection and self-analysis of the substance to be analyzed.

Figure 9:
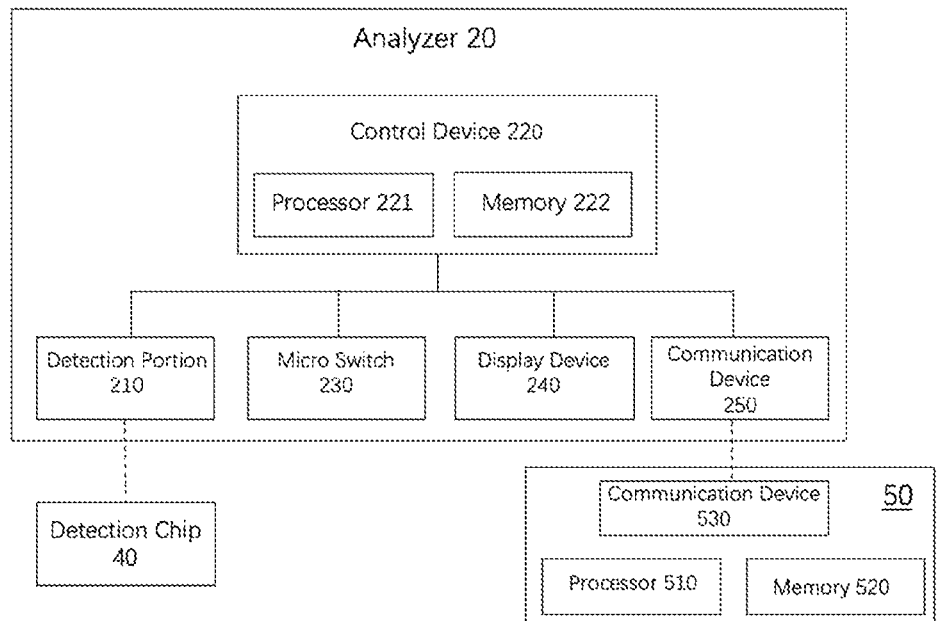
FIG. 9 is a schematic block diagram of an analyzer provided by some embodiments of the present disclosure.

FIG. 9 is a schematic block diagram of an analyzer provided by some embodiments of the present disclosure.

For example, as illustrated in FIG. 9, the analyzer 20 includes a detection portion 210, a control device 220, at least one micro switch 230, a display device 240, and at least one communication device 250.

For example, the detection portion 210 is configured to perform detection on the detection chip 40 and receive detection data of the detection chip 40.

For example, the detection portion 210 may include a light source and a dedicated or general-purpose circuit, chip or device. For example, the detection portion 210 may include a photoelectric detection circuit board or the like to achieve detection of optical parameters of the substance to be analyzed contained in the detection chip 40. For example, the detection portion 210 may refer to the corresponding description about the detection portion 104 of the analyzer 110 in the above-mentioned embodiments.

For example, the control device 220 is configured to determine whether an analysis parameter corresponding to the detection chip 40 used for detection is obtained and request to obtain the analysis parameter in a case where the analysis parameter is not obtained, and the control device 220 is further configured to, in a case of being determined that the analysis parameter is obtained, allow the detection portion 210 to perform detection on the detection chip 40 to obtain the detection data, and analyze the detection data by using the analysis parameter to obtain analysis data of a substance to be analyzed contained in the detection chip 40.

For example, the control device 220 is further configured to detect an operation applied to a micro switch 230 and generate a control signal according to the operation. The control signal is used for the interaction process of the analyzer 20.

For example, the micro switch 230 protrudes outwards from a surface of the analyzer 20 and has a long strip shape, and the micro switch 230 is configured to be capable of being operated in at least two directions. The control device 220 is further configured to generate different control signals for interaction according to operations of the micro switch 230 in different directions. For example, the micro switch 230 may refer to the corresponding description of the micro switch 112 of the analyzer 10 in the above-mentioned embodiments.

For example, the display device 240 is configured to display the analysis data or display different interactive operation interfaces according to the control signal.

For example, the display device 240 may be any component with a display function, such as a liquid crystal panel, an OLED panel, an electronic paper display device, etc., and the embodiments of the present disclosure are not limited in this aspect.

For example, the communication device 250 includes a communication interface and is configured to allow the analyzer 20 to be in signal connection with a parameter storage device or a mobile terminal, such as a second mobile terminal 50, so as to allow the analyzer 20 to receive a control signal provided by the second mobile terminal 50 or allow the analyzer 20 to provide the analysis data to the second mobile terminal 50. For example, the analyzer 20 may include two communication devices, wherein the first communication device includes a communication interface used for signal connection with the parameter storage device to obtain the analysis parameter, and the second communication device is used for connection with a mobile terminal to achieve online detection. The two communication devices are of different types, for example, the first communication device is a USB device, which also has a charging function, while the second communication device is a wireless communication device, which does not have a charging function. In the case where the parameter storage device is also a mobile terminal, the analyzer 20 may include one communication device, which is used for obtaining the analysis parameter and online detection.

For example, the signal connection between the analyzer 20 and the second mobile terminal 50 can be established through the communication device 250 of the analyzer 20 and the communication device 530 of the second mobile terminal 50.

For example, the communication device 250 and the communication device 530 may be dedicated or general-purpose circuits, chips or devices, and the embodiments of the present disclosure are not limited thereto.

For example, the second mobile terminal 50 further includes a processor 510 and a memory 520, and the memory 520 includes one or more computer program modules. The one or more computer program modules are stored in the memory 520 and configured to be executed by the processor 510, and the one or more computer program modules include instructions for transmitting the control signal to the analyzer 20 or receiving and storing the analysis data provided by the analyzer 20.

For example, the processor 510 may be a central processing unit (CPU), a digital signal processor (DSP), or other processing units with data processing capability and/or program execution capability, such as a field programmable gate array (FPGA). For example, the central processing unit (CPU) may be X86 or ARM architecture. The processor 510 may be a general-purpose processor or a special-purpose processor, and may control other components in the second mobile terminal 50 to perform desired functions.

For example, the memory 520 may include any combination of one or more computer program products, which may include various forms of computer-readable storage media, such as the volatile memory and/or nonvolatile memory. For example, the volatile memory may include a random access memory (RAM) and/or cache. The nonvolatile memory may include such as the read-only memory (ROM), hard disk, erasable programmable read-only memory (EPROM), portable compact disk read-only memory (CD-ROM), USB memory, flash memory, or the like. One or more computer program modules may be stored on the computer-readable storage medium, and the processor 510 may execute the one or more computer program modules to achieve various functions of the second mobile terminal 50. The computer-readable storage medium may also store various applications and data as well as data used and/or generated by the applications.

For example, the analyzer 20 also includes a communication interface, which is located on a surface of the analyzer 20 and is configured to establish the signal connection between the analyzer 20 and the parameter storage device that stores the analysis parameter, so that the analyzer can read and store the analysis parameter. For example, the communication interface may refer to the communication interface 111 illustrated in FIG. 6.

For example, the communication interface may be a USB interface or a wireless communication interface.

For example, the communication interface may also be configured to charge the analyzer 20.

For example, the parameter storage device may also be implemented by the second mobile terminal 50, that is, the parameter storage device and the second mobile terminal 50 can be the same equipment with a storage function, and the embodiments of the present disclosure are not limited in this aspect.

For example, the detection portion 210, the micro switch 230, the display device 240, and the communication device 250 may all be in signal connection with the control device 220.

For example, the control device 220 includes a processor 221 and a memory 222, and the memory 222 includes one or more computer program modules. The one or more computer program modules are stored in the memory 222 and configured to be executed by the processor 221, and the one or more computer program modules include instructions for implementing the control method of the analyzer provided by any one of the embodiments of the present disclosure.

For example, the processor 221 may be a central processing unit (CPU), a digital signal processor (DSP), or other processing units with data processing capability and/or program execution capability, such as a field programmable gate array (FPGA). For example, the central processing unit (CPU) can be X86 or ARM architecture. The processor 221 may be a general-purpose processor or a special-purpose processor, and may control other components in the control device 220 or other components in the analyzer 20 to perform desired functions.

For example, the memory 222 may include any combination of one or more computer program products, which may include various forms of computer-readable storage media, such as the volatile memory and/or nonvolatile memory. For example, the volatile memory may include a random access memory (RAM) and/or cache. The nonvolatile memory may include such as the read-only memory (ROM), hard disk, erasable programmable read-only memory (EPROM), portable compact disk read-only memory (CD-ROM), USB memory, flash memory, or the like. One or more computer program modules may be stored on the computer-readable storage medium, and the processor 221 may execute the one or more computer program modules to achieve various functions of the analyzer 20. The computer-readable storage medium may also store various applications and data as well as data used and/or generated by the applications. The specific functions and technical effects of the analyzer 20 may refer to the above description about the control method of the analyzer, and details are not described herein again.

It should be noted that, in the embodiments of the present disclosure, the control device 220 may be hardware, software, firmware, and any feasible combination thereof. For example, the control device 220 may be a dedicated or general circuit, chip or device, or a combination of a processor and a memory. The embodiments of the present disclosure do not limit the specific implementation form of the control device 220.

For example, the functions or technical effects of the analyzer provided by the embodiments of the present disclosure may refer to the corresponding descriptions of the control method of the analyzer in the above embodiments, and details are not described herein again.

It should be noted that the analyzer 20 may also include other components, such as a supporting portion, a photoelectric signal conversion circuit, etc. These components may adopt existing conventional components, and details are not described herein again.

At least one embodiment of the present disclosure further provides a detection system, which includes at least one detection chip and the analyzer provided by any one of the embodiments of the present disclosure, for example, may include the analyzer 110 or the analyzer 20 in the above embodiments.

For example, at least one detection chip can be built into the analyzer when in use.

At least one embodiment of the present disclosure further provides a detection system, which includes an analyzer, at least one detection chip, and a parameter storage device provided by any one of the embodiments of the present disclosure, for example, may include the analyzer 110 or the analyzer 20, the detection chip 130 or the detection chip 40, and the parameter storage device 120 in the above embodiments. The parameter storage device stores the analysis parameter, and is configured to be in signal connection with the analyzer through the communication interface of the analyzer, so that the analyzer can read and store the analysis parameter.

For example, the parameter storage device provided by the embodiments of the present disclosure can be any product or component with a storage function, such as a USB flash memory mover, a hard disk, a floppy disk, an optical disk, a mobile phone, a tablet computer, a notebook computer, a digital photo frame, a navigator, a contact IC card, a non-contact IC card, etc. The embodiments of the present disclosure are not limited thereto.

At least one embodiment of the present disclosure further provides a storage medium for storing non-transitory computer readable instructions, and the control method of the analyzer according to any one of the embodiments of the present disclosure is implemented upon the non-transitory computer readable instructions being executed by a computer.

Figure 10:
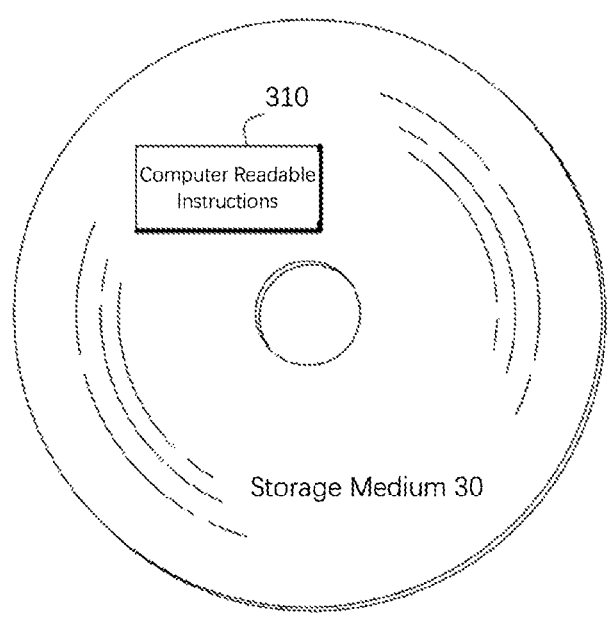
FIG. 10 is a schematic diagram of a storage medium provided by some embodiments of the present disclosure.

FIG. 10 is a schematic diagram of a storage medium provided by some embodiments of the present disclosure.

For example, as illustrated in FIG. 10, the storage medium 30 is used to store non-transitory computer readable instructions 310. For example, upon the non-transitory computer readable instructions 310 being executed by a computer, one or more steps in the control method of the analyzer according to the above-described embodiments can be performed.

For example, the storage medium 30 may be the memory 222 in the analyzer 20 illustrated in FIG. 9, and the corresponding description about the memory 222 in the analyzer 20 illustrated in FIG. 9 may be referred to, which will not be repeated herein.

For the present disclosure, the following statements should be noted:

(1) The accompanying drawings related to the embodiment(s) of the present disclosure involve only the structure(s) in connection with the embodiment(s) of the present disclosure, and other structure(s) can be referred to common design(s).

(2) In case of no conflict, features in one embodiment or in different embodiments can be combined to obtain new embodiments.

What have been described above merely are specific implementations of the present disclosure, and the protection scope of the present disclosure is not limited thereto. The protection scope of the present disclosure should be based on the protection scope of the claims.

What is claimed is:

1. A control method of an analyzer, wherein the analyzer is configured to perform detection on a detection chip based on an analysis parameter, the detection chip is configured to contain a substance to be analyzed for detection and analysis, and the control method comprises:
   determining whether the analyzer obtains the analysis parameter corresponding to the detection chip used for detection;
   requesting and obtaining the analysis parameter in a case of being determined that the analyzer does not obtain the analysis parameter; and
   performing detection on the detection chip and analyzing the substance to be analyzed contained in the detection chip by using the analysis parameter to obtain analysis data of the substance to be analyzed in a case of being determined that the analyzer obtains the analysis parameter,
   wherein the analyzer further comprises at least one micro switch, and the control method further comprises:
   detecting an operation applied to the micro switch, and generating a control signal according to the operation, wherein the control signal is used for an interaction process of the analyzer.

2. The control method of the analyzer according to claim 1, wherein the analyzer comprises a communication interface, and obtaining the analysis parameter comprises:
   allowing the analyzer to establish signal connection with a parameter storage device storing the analysis parameter through the communication interface, and reading and storing the analysis parameter.

3. The control method of the analyzer according to claim 2, wherein the parameter storage device is a USB flash drive and the communication interface is a USB interface; or the parameter storage device is a first mobile terminal, and the communication interface is a wireless communication interface.

4. The control method of the analyzer according to claim 2, wherein the parameter storage device comprises a housing and further comprises a control circuit and a memory provided in the housing,
   the analysis parameter is stored in the memory, and the control circuit is configured to establish the signal connection and read the analysis parameter from the memory.

5. The control method of the analyzer according to claim 1, wherein, in the case of being determined that the analyzer obtains the analysis parameter, the control method further comprises:
   prompting to check whether the analysis parameter currently obtained corresponds to the detection chip used for detection; and
   requesting to obtain a new analysis parameter in a case where the analysis parameter currently obtained does not correspond to the detection chip used for detection.

6. The control method of the analyzer according to claim 1, wherein the analysis parameter comprises a calculation curve for acquiring the analysis data based on detection data of the detection chip.

7. The control method of the analyzer according to claim 1, wherein the micro switch protrudes outwards from a surface of the analyzer and has a long strip shape, and the micro switch is configured to be capable of being operated in at least two directions; and
   the generating the control signal according to the operation comprises:
   generating different control signals for interaction according to operations of the micro switch in different directions.

8. The control method of the analyzer according to claim 1, wherein the analyzer further comprises a display device, and the control method further comprises:
   displaying the analysis data through the display device, or allowing the display device to display different interactive operation interfaces according to the control signal.

9. The control method of the analyzer according to claim 8, wherein the analysis data comprises a plurality of items, and the displaying the analysis data through the display device comprises:
   switching a display page of the display device according to the control signal so as to display different items in the analysis data.

10. The control method of the analyzer according to claim 1, wherein the analyzer further comprises a communication device, and the control method further comprises:
    allowing the analyzer to be in signal connection with a second mobile terminal through the communication device, and receiving the control signal provided by the second mobile terminal or providing the analysis data to the second mobile terminal.

11. The control method of the analyzer according to claim 10, further comprising:
    determining whether to establish the signal connection between the analyzer and the second mobile terminal through the communication device, and selecting an operation mode.

12. The control method of the analyzer according to claim 10, wherein the second mobile terminal comprises a display function, and the control method further comprises:

displaying the analysis data and/or an analysis result provided based on the analysis data through the second mobile terminal, or displaying an interactive operation interface through the second mobile terminal for generating the control signal.

13. The control method of the analyzer according to claim 1, further comprising:

performing equipment detection on the analyzer to determine whether the analyzer satisfies a condition for performing detection on the detection chip.

14. The control method of the analyzer according to claim 1, wherein the substance to be analyzed comprises a breast milk sample.

15. A storage medium, used for storing non-transitory computer readable instructions, wherein the control method of the analyzer according to claim 1 is implemented upon the non-transitory computer readable instructions being executed by a computer.

16. An analyzer, comprising a detection portion and a control device, wherein the detection portion is configured to perform detection on a detection chip and receive detection data of the detection chip;

the control device is configured to determine whether an analysis parameter corresponding to the detection chip used for detection is obtained and request to obtain the analysis parameter in a case where the analysis parameter is not obtained, and the control device is further configured to, in a case of being determined that the analysis parameter is obtained, allow the detection portion to perform detection on the detection chip to obtain the detection data, and analyze the detection data by using the analysis parameter to obtain analysis data of a substance to be analyzed contained in the detection chip; and the analyzer further comprises at least one micro switch, and the control device is further configured to generate a control signal according to an operation applied to the micro switch, wherein the control signal is used for an interaction process of the analyzer.

17. The analyzer according to claim 16, wherein the control device comprises:

a processor; and a memory, comprising one or more computer program modules, wherein the one or more computer program modules are stored in the memory and configured to be executed by the processor, and the one or more computer program modules comprise instructions for implementing a control method of the analyzer, wherein the analyzer is configured to perform detection on the detection chip based on the analysis parameter, the detection chip is configured to contain the substance to be analyzed for detection and analysis, and the control method comprises:

determining whether the analyzer obtains the analysis parameter corresponding to the detection chip used for detection;

requesting and obtaining the analysis parameter in a case of being determined that the analyzer does not obtain the analysis parameter; and performing detection on the detection chip and analyzing the substance to be analyzed contained in the detection chip by using the analysis parameter to obtain the analysis data of the substance to be analyzed in a case of being determined that the analyzer obtains the analysis parameter.

18. A detection system, comprising the analyzer according to claim 16 and at least one detection chip.

19. A detection system, comprising the analyzer according to claim 16, at least one detection chip, and a parameter storage device, wherein the parameter storage device stores the analysis parameter and is configured to be in signal connection with the analyzer through a communication interface of the analyzer, so as to allow the analyzer to read and store the analysis parameter.

* * * * *